United States Patent
Tian et al.

(10) Patent No.: US 9,801,919 B2
(45) Date of Patent: Oct. 31, 2017

(54) ORAL COMPOSITIONS CONTAINING ENHANCED ANTIBACTERIAL COMBINATIONS OF ANTIOXIDANTS AND EXTRACTS OF MAGNOLIA

(75) Inventors: Minmin Tian, Naperville, IL (US); Michael W. Dodds, La Grange Park, IL (US); Michael J. Greenberg, Northbrook, IL (US)

(73) Assignee: WM. WRIGLEY JR. COMPANY, Chicago, IL (US)

( * ) Notice: Subject to any disclaimer, the term of this patent is extended or adjusted under 35 U.S.C. 154(b) by 533 days.

(21) Appl. No.: 12/994,359

(22) PCT Filed: May 26, 2009

(86) PCT No.: PCT/US2009/045126
§ 371 (c)(1),
(2), (4) Date: Feb. 18, 2011

(87) PCT Pub. No.: WO2009/148875
PCT Pub. Date: Dec. 10, 2009

(65) Prior Publication Data
US 2011/0129426 A1    Jun. 2, 2011

Related U.S. Application Data

(60) Provisional application No. 61/057,501, filed on May 30, 2008.

(51) Int. Cl.
*A61K 36/575* (2006.01)
*A61K 31/05* (2006.01)
*A61K 31/216* (2006.01)

(52) U.S. Cl.
CPC ............ *A61K 36/575* (2013.01); *A61K 31/05* (2013.01); *A61K 31/216* (2013.01)

(58) Field of Classification Search
CPC ..... A61K 36/575; A61K 6/0067; A61K 31/05
See application file for complete search history.

(56) References Cited

U.S. PATENT DOCUMENTS 4,291,045 A * 9/1981 Mackay et al. ................ 514/373
2006/0140885 A1* 6/2006 Gaffar et al. .................... 424/58

FOREIGN PATENT DOCUMENTS

| FR | 2773811 | * | 7/1999 |
| JP | 1151512 | | 6/1989 |
| JP | 2001010904 | | 1/2001 |
| WO | 0182922 | | 11/2001 |
| WO | 02/081024 A1 | | 10/2002 |
| WO | 2007064505 | | 6/2007 |

OTHER PUBLICATIONS

Kubo et al. Bioorganic & Medicinal Chemistry Letters 12 (2002) 113-116.*
Kubo et al.—Journal of Natural Products. vol. 55, No. 6, pp. 780-785, Jun. 1992.*
Simonetti et al. J Chemother. Apr. 2004;16(2):122-7.*
Konaté et al. Annals of Clinical Microbiology and Antimicrobials 2012, 11:18.*
MC Berenbaum (The Journal of Infections Diseases. vol. 137, No. 2; Feb. 1978:122-130).*
Mukherjee et al. (Clinical Microbiology Reviews, Jan. 2005, p. 163-194).*
Grinda, Robert Jean. FR2773811. MAchine Translation to English. Jul. 1999.*
Su et al. Yaoxue Xuebao, v. 37, (11), Nov. 2002, p. 870-875. Abstract.*
Wei Zeying et al., J of Chongqing University. vol. 8(3). 2015. pp. 154-158.*
L.I. Kupp, S. Rosen and F.M. Beck; Effect of Anti-oxidants on Growth and Lactic Acid Production by *Streptococcus* mutans; Jul. 1985; pp. 1016-1018; The Ohio State University College of Dentistry; Columbus, OH.
G. Simonetti, N. Simonetti, A. Villa; Increased Microbicidal Activity of Green Tea (*Camellia sinensis*) in Combination with Butylated Hydroxyanisole; Journal of Chemotherapy; 2004; vol. 16, n. 2 (122-127); Edizioni Riviste Scientifiche.

* cited by examiner

Primary Examiner — Jeffrey S Lundgren
Assistant Examiner — Chris Simmons

(57) ABSTRACT

An oral composition contains an enhanced antibacterial effective amount of an antioxidant and an extract of *Magnolia*.

17 Claims, No Drawings

ORAL COMPOSITIONS CONTAINING ENHANCED ANTIBACTERIAL COMBINATIONS OF ANTIOXIDANTS AND EXTRACTS OF MAGNOLIA

CROSS-REFERENCE TO RELATED APPLICATIONS

This invention claims priority to U.S. Provisional Patent Application Ser. No. 61/057,501, filed May 30, 2008, which is herein incorporated by reference.

BACKGROUND OF THE INVENTION

This invention relates to an antibacterial combination of an antioxidant and an extract of *Magnolia officinalis*, and more particularly, to an oral composition containing such combination which exhibits increased oral care effects against *Streptococcus mutans*, a bacterium associated with dental caries.

Compounds such as chlorhexidine, benzothonium chloride and cetyl pyridinium chloride have been used in the art as antibacterial agents in oral compositions. However, such agents experience reduced effectiveness when in presence of an anionic surfactant required for the effective performance of oral compositions such as toothpaste and mouthrinses. In contrast, noncationic antibacterial materials are compatible with anionic surfactants in oral compositions and noncationic halogenated hydroxydiphenyl ethers such as Triclosan have been effectively employed in commercial oral compositions. Notwithstanding the efficacy of such antibacterial compounds, many of these compounds are regulated by both the U.S. Food and Drug Administration and by the European Union making their applications into food and confections for oral care usage quite limited. Further, aside from their product deployment challenges relating to interactions with other ingredients and efficacy, these compounds often impart other unpleasant characteristics, including but not limiting to poor taste, potential tooth discoloration and mouth irritation to sensitive oral tissues.

Recently, interest has been generated in the medicinal properties of herbal preparations for use in oral compositions. Herbal preparations are considered "more natural" and are therefore viewed as more acceptable antibacterial ingredients to the consumer.

Extracts of *Magnolia* Cortex (barks of *Magnolia officinalis*) are known to have antibacterial efficacy. For example, it has been reported in "Dental caries Prevention by Traditional Chinese Medicines", T. Namba et al, J. Medicinal Plant Res., vol. 44, pp. 100-106 (1982) that some active principles of these extracts, identified to be magnolol and honokiol, were bactericidal against *S. mutans* in the in vitro test Minimal Inhibitory Concentration (MIC). Unfortunately at high concentrations, *magnolia* has the potential to discolor teeth, and impart unfavorable taste characteristics; thus, providing low and efficacious levels would be more appealing and beneficial to consumers.

The dental art is continuously seeking enhanced efficacy of antibacterial compounds. An advantage of such enhancement is that the effectiveness increases, and lower quantities of the antibacterial agent are required to achieve the desired therapeutic effect while providing great taste, lower cost, and meet regulatory guidelines. Such combinations also are particularly important in the treatment of delicate or sensitive tissues, such as the oral mucosa reducing the likelihood of ulceration of oral mucous membranes, induction of desquamative gingivitis, and discoloration.

Thus, there is a recognized need for, and it would be highly advantageous, to have an antibacterial oral composition in which a combination of an antioxidant and an extract of *Magnolia* cortex exhibited enhanced antibacterial activity against *Streptococcus mutans* (*S. mutans*) and thereby for enhanced effectiveness against dental caries.

SUMMARY OF THE INVENTION

An oral composition contains an enhanced antibacterial-effective amount of an antioxidant and an extract of *Magnolia*.

DESCRIPTION OF THE INVENTION

Dental caries is an infectious disease which damages the structures of teeth. Tooth decay or cavities are consequences of caries. If left untreated, the disease can lead to pain, tooth loss, infection, and, in severe cases, death of the tooth. There are numerous ways to classify dental caries. Although the presentation may differ, the risk factors and development among distinct types of caries remain largely similar.

Tooth decay is recognized as caused by certain types of acid-producing bacteria, for example, *Streptococcus mutans* (Gram-positive, facultatively anaerobic bacteria commonly found in the human oral cavity), which cause damage in the presence of fermentable carbohydrates such as sucrose, fructose, and glucose. The resulting high levels of acidity from lactic acid in the mouth affect teeth because a tooth's special mineral content causes it to be sensitive to low pH. Specifically, a tooth (which is primarily mineral in content) is in a constant state of back-and-forth demineralization and remineralization between the tooth and surrounding saliva. When the pH at the surface of the tooth drops below 5.5, demineralization proceeds faster than remineralization (i.e. there is a net loss of mineral structure on the tooth's surface). This results in the ensuing decay. Depending on the extent of tooth destruction, various treatments can be used to restore teeth to proper form, function, and aesthetics, but there is no known method to regenerate large amounts of tooth structure. Instead, dental health organizations advocate preventive and prophylactic measures, such as regular oral hygiene and dietary modifications, to avoid dental caries.

An oral composition of the present invention can take any physical form suitable for application to an oral surface and provides either a cosmetic prophylactic or therapeutic benefit within or derived from the oral cavity. In various embodiments, an oral composition of this invention can be a dentifrice such as a powder or paste; an edible film or bioadhesive film; a confectionary composition including but not limiting to breath mints, low boiled candy, chewing gum, chewy candy, hard boiled candy, coated candy, lozenges, syrups, pressed mints, throat drops, chocolates and the like. In certain embodiments, the consuming or masticating of the oral composition may be repeated at regular intervals.

As used herein, the term "efficacious" means producing or capable of producing a desired effect. When used in respect to an "effective amount" refers to the level, amount, serving, or percent which produces or is capable of producing a desired effect. All percentages and ratios used herein are by weight of the total composition and all measurements made are at 25° C., unless otherwise designated.

An "antioxidant" useful in this invention is a compound capable of slowing or preventing oxidation of other compounds. Oxidation is a chemical reaction that transfers electrons from a substance to an oxidizing agent. Oxidation reactions can produce free radicals, which start chain reactions which may damage cells. Antioxidants typically terminate these chain reactions by removing free radical intermediates, and inhibit other oxidation reactions by being oxidized themselves. As a result, antioxidants are often reducing agents such as thiols or polyphenols. Antioxidants containing a phenolic group are known to be natural antioxidants and may be added constituents in food products. An antioxidant may be natural, synthetic or semi-synthetic.

An "antibacterial" or "antibacterial agent" is a compound that acts against bacteria. For the purposes of the present invention, useful antibacterial agents are specific to killing or inhibiting growth of Streptococcus mutans (S. mutans) or Streptococcus sobrinus (S. sobrinus).

Antioxidants useful in this invention are food-acceptable substances which possess antioxidant properties. Among useful antioxidants are natural and synthetic substances. Preferable antioxidants useful in this invention are phenolic compounds or derivatives of phenolic compounds. As used in this invention, a phenolic compound includes hydroxy-substituted aromatic compounds (such as a phenol (hydroxy benzene)) and further includes unsaturated cyclic carbon and carbon-oxygen compounds substituted with at least on ring hydroxy or hydroxy derivative (an example of which are derivatives of ascorbic acid).

Many naturally occurring substances possess antioxidant capabilities. A class of widely used natural antioxidant is tocopherols. Recently, extracts of some spices such as rosemary, also have been successfully and commercially exploited as natural antioxidants. Other naturally occurring antioxidants are coniferyl alcohol and guaiaconic and guaiccic acid (from gum guaiac). As described herein, the term "natural" means a chemical compound or substance produced by a living organism and found in nature, which may possess a pharmacological or biological activity for use in pharmaceutical drug discovery and drug design. A product may be considered as "natural" although the product is prepared by total synthesis if the components are substantially identical to a substance found in nature.

Typically, naturally-occurring antioxidants useful in this invention are structurally related to synthetically-made phenolic compounds such as butylated hydroxyanisole (BHA), butylated hydroxytoluene (BHT), propyl gallate, octyl gallate, dodecyl gallate, ascorbyl palmitate, and di-t-butylhydroquinone (TBHQ) and combinations thereof. Compounds containing phenolic moieties as part of their molecular structure, promote antibacterial activity when present in oral compositions in orally-acceptable amounts in compositions of this invention.

Surprisingly, certain combinations of antioxidants and extracts of magnolia against Streptococcus mutans (S. mutans) have been found to enhance effectiveness (act synergistically) against dental caries. Preferable antioxidants having enhanced (synergistic) antibacterial effects in combination with Magnolia Extract against S. mutans include but are not limited to butylated hydroxyanisole (BHA), propyl gallate, octyl gallate, and dodecyl gallate.

Compositions useful in the present invention comprise extract of magnolia ("magnolia extract"). As referred to here, such an "extract" of magnolia is an extract from dried cortex, or bark, of a plant from the Magnoliaceae family, such as Magnolia officinalis, ("magnolia") or a synthetic or semi-synthetic equivalent of such an extract or an active component or compound thereof. Typically, extracts of Magnolia Cortex (the bark of Magnolia officinalis) contain active compounds including magnolol, honokiol, tetrahydromagnolol, and tetrahydrohonokiol, which have demonstrated bactericidal properties against S. mutans by in vitro Minimal Inhibitory Concentration (MIC) testing. Any plant from the Magnoliaceae family is suitable for the present invention and may be used in alternate embodiments, preferably such that the extract comprises an antibacterial-effective concentration of a compound selected from the group consisting of magnolol, honokiol, tetrahydromagnolol, tetrahydrohonokiol, and mixtures thereof.

As used herein, "extracting" or "extraction" of a solid or liquid material means contacting the material with an appropriate solvent to remove the substance(s) desired to be extracted from the material. Where the material is solid, it is preferably dried and crushed or ground prior to contacting it with the solvent. Such an extraction may be carried out by conventional means known to one of skill in the art, for example, by using an extraction apparatus, such as a Soxhlet apparatus, which retains the solid material in a holder and allows the solvent to flow through the material; or by blending the solvent and material together and then separating the liquid and solid phases or two immiscible liquid phases, such as by filtration or by settling and decanting.

In one embodiment, magnolia extract is made from dried Magnolia plant bark and can be prepared by extracting the bark using an appropriate solvent. Solvents include compatible liquids such as hydrocarbons and substituted hydrocarbons containing up to about 20 carbon atoms, such as alkanes, alcohols, halogenated alkanes, ethers, and the like, and specifically including methanol, ethanol, methylene chloride, hexane, cyclohexane, pentane, petroleum ether, chloroform, ethylene dichloride, and hydrofluoroalkanes, such as 1,1,1,2-tetrafluoroethane (HFA-13A). Generally, one part of plant tissue (dry basis) is extracted with about 5 to about 50 parts, preferably about 15 parts to about 30 parts of solvent using an extraction apparatus where the solvent is contacted with the bark to obtain a concentrated paste which is then subjected to one or more additional extraction steps with different solvents to further concentrate the originally obtained paste over an extended period of time, preferably about 6 to 48 hours, more preferably for about one day. In one simplified method of extraction, the dried, crushed Magnolia bark in the form of a powder is contacted with a hydrofluoroalkane (such as, 1,1,1,2-tetrafluoroethane (HFA-13A)) to form a concentrated final extraction yielding an extract containing about 5 to about 50% honokiol and about 5 to about 50% magnolol.

In preferred embodiments, the natural extract active ingredients used in oral compositions are reproducible, stable, and have microbiological safety. In one embodiment of the present invention, the magnolia extract is isolated by supercritical fluid extraction (SFE) using carbon dioxide ($CO_2$). Supercritical fluids are gases with properties between that of a "normal" phase of gas and liquid. Pressure variations control the properties of the supercritical fluids, which can range from more gas-like behavior to more liquid-like behavior, depending on the application. Supercritical fluids use a solvent that is readily available, inexpensive, and environmentally safe (such as $CO_2$). Carbon dioxide is non-toxic, non-explosive, readily available and easily removed from the extracted products. Process temperatures for SFE are generally low to moderate. Thus, SFE produces nearly solvent-free products, and further avoid any potential deterioration reactions.

Natural contaminants which may be potentially present in other extraction methodologies are generally absent in the SFE extracted product. For example, compounds such as aristocholic acid and alkaloids, such as magnocurine and tubocurarine, are kept at low concentrations (for example, generally less than 0.0002 percent). Thus, in the embodiment where the *magnolia* is extracted by SFE, the extract is substantially free from chemical alterations brought about by heat and water, from solvent residues, and other artifacts.

Further, certain SFE *magnolia* extracts are cosmetically acceptable. Certain methods of *magnolia* extraction produce a dark brown product that is difficult to formulate in an oral composition, due to the dark color, even at low concentrations. In certain embodiments, SFE extraction produces a much lighter color of *magnolia* extract (a light beige product) that is particularly suitable for aesthetically pleasing oral composition formulations.

In various embodiments, it is preferred that the active antibacterial ingredient comprises either magnolol, honokiol, or both. Magnolol and honokiol are non-ionic hydroxybiphenyl compounds, the structures of which are believed to be as follows:

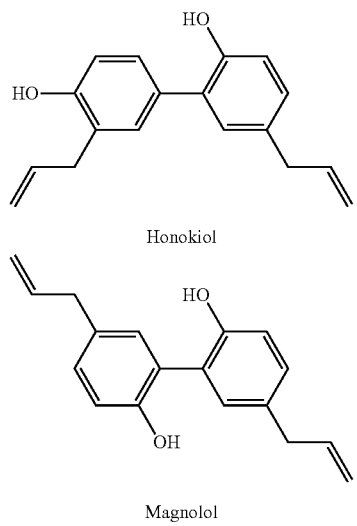

Honokiol

Magnolol

Additionally, tetrahydromagnolol and tetrahydrohonokiol are hydrogenated analogs of magnolol and honokiol often found in relatively small concentrations in the extracts of *magnolia*, and as such may be included in the antibacterial composition.

Thus, as will be described in greater detail below, in various embodiments of the present invention, an effective amount of *magnolia* extract comprises one or more active compounds: magnolol, honokiol, tertrahydromagnolol and tetrahydrohonokiol and mixtures thereof, which are used in combination with an antioxidant to inhibit or kill *S. mutans* (associated with dental caries) present in the oral cavity.

*Magnolia* extracts useful in this invention are commercially available. One such extract is obtained by supercritical carbon dioxide extraction, comprising a total content of magnolol higher than 90%.

To evaluate an enhanced effect of an active ingredient in combination of *magnolia* with antioxidant, the fractional inhibitory index (FIC) is computed according to equation (1):

$$FIC = \frac{MIC(A \text{ combined with } B)}{MIC(A \text{ alone})} + \frac{MIC(B \text{ combined with } A)}{MIC(B \text{ alone})} \quad (1)$$

where the Minimum Inhibitory Concentration (MIC) was determined using the microtiter format according to the standard procedures (Manual of Clinical Microbiology, 1995) and was used to determine whether the antibacterial efficacy of the *magnolia* extract antioxidant combination exhibited enhanced activity when the FIC value of less than 1.0 is enhanced (synergistic), an FIC between 1.0 and 2.0 is additive, and an FIC greater than 2.0 is antagonistic.

An enhanced effective amount of *magnolia* extract in combination with an antioxidant will have a fractional inhibitory concentration (FIC) of less than 1 against *S. mutans*.

In various embodiments, *magnolia* extract of the present invention comprises magnolol, honokiol, or both in an amount of about 2 wt. % to about 99 wt. %. In other embodiments, *magnolia* extract comprises magnolol, honokiol, or both in an amount greater than 50 wt. %. In one embodiment of the present invention, the magnolol is present in an amount greater than 50 wt. %, greater than 70 wt. % or most preferably, greater than 90 wt. %. In another embodiment, honokiol is present in an amount less than 50 wt. %, more preferably in an amount less than 30 wt. %, or most preferably, less than 10 wt. %.

An effective concentration of *magnolia* extract and antioxidant in an oral composition of this invention depends upon the relative concentration at which enhancement of antibacterial activity against *S. mutans* is achieved.

In an aspect of the invention, an enhanced activity antibacterial weight ratio of *magnolia* extract to antioxidant against *S. mutans* in an oral composition is at least 0.1:1, typically at least 0.5:1 and preferably at least 1:1. This weight ratio may range up to 1:100 or above, typically up to 1:50, preferably up to 1:10. A typical weight ratio range is between 0.5:1 to about 1:10 and preferably 1:1 to 1:5). Preferably, the ratio of *magnolia* extract to antioxidant is between 1:1 to about 1:5 wherein the antioxidant is selected from the group consisting of butylated hydroxyanisole (BHA), propyl gallate, octyl gallate, and dodecyl gallate In other embodiments of the present invention, *magnolia* extract is present in the oral composition in an amount of about 0.001 to about 5 wt. %. Such a concentration is dependent upon the concentration of the antioxidant employed for enhanced antibacterial results against *S. mutans*. In one embodiment, *magnolia* extract is present in the oral composition in an amount of about 0.001 to about 3 wt. %. In other embodiments, the *magnolia* extract is present at less than 1 wt. %, for example the extract is present at a concentration of in an amount of about 0.01 to about 1 wt. %. In one preferred embodiment, the *magnolia* extract is present in the oral composition at a concentration of about 0.02 wt. %. More preferably, the concentration of *magnolia* extract is below a level which produces a discoloration on teeth and most preferably below a level which produces an objectionable taste.

Still further, the antioxidant is present in the oral composition in an amount of about 0.001 to about 5 wt. %. Such a concentration is dependent upon the concentration of the *magnolia* extract employed for synergistic antibacterial results against *S. mutans*. In one embodiment, the *magnolia* extract is present in the oral composition in an amount of about 0.001 to about 3 wt. %. In other embodiments, the *magnolia* extract is present at less than 1%, for example the extract is present at a concentration of in an amount of about 0.01 to about 1 wt. %. In one preferred embodiment, the *magnolia* extract is present in the oral composition at a concentration of about 0.02 wt. %. *Magnolia* extract content may be determined by High Performance Liquid Chromatography (HPLC).

While not limiting to theories by which the present invention is bound, it is generally believed that a minimum enhanced effective antibacterial level (Minimum Inhibitory Concentration) of *magnolia* extract (as measured by magnolol, honokiol, or the combination of both active compounds) is between about 5 µg/mL (5 mg/kg or parts per million (ppm)) to about 20 µg/mL (20 ppm) and the antioxidant concentration is between 50 µg/mL to about 70 µg/mL against *S. mutans* in an oral composition.

In a preferred embodiment, an effective enhanced antibacterial level against *S. mutans* of *magnolia* extract is between 10 µg/mL to about 15 µg/mL and the antioxidant is selected from the group consisting of butylated hydroxyanisole (BHA), propyl gallate, octyl gallate, and dodecyl gallate wherein the level of antioxidant is between 55 µg/mL to about 65 µg/mL.

I. Data

The following tests were conducted on *S. mutans*.

BHA, gallic acid, octyl gallate and *magnolia* bark extract (MBE) sample were dissolved in ethanol to produce 1-10% working solution and was added to a nutrient broth and shaken well and was diluted two-fold in individual test tubes. A total of 0.2 milliliter (mL) of inoculated bacteria culture purchased from American Type Culture Collection (ATCC) was added to each test tube. The tubes were incubated aerobically at 37° C. for 1 to 2 days. The MIC level was recorded as the lowest concentration of test compound that showed no visible growth. FIC values were determined by equation 1.

TABLE 1

MIC and FIC values of MBE and common antioxidants against *S. mutans*

| Sample | MIC (ppm) | FIC |
|---|---|---|
| MBE | 25 | — |
| BHA | 250 | — |
| Gallic acid | >2000 | — |
| Octyl gallate | 250 | — |
| MBE/BHA - (1:5) | 12.5/62.5 | 0.75 |
| MBE/Octyl gallate (1:5) | 12.5/62.5 | 0.75 |
| MBE/Gallic acid (1:10) | 25/250 | 1.0 |

In review of the results, BHA and octyl gallate respectively appear to have an enhanced effect with MBE having a FIC value of 0.75. An additive effect was seen when MBE and gallic acid were combined.

For comparison, tests were conducted on *Streptococcus sobrinus* (*S. sobrinus*) to see if the results demonstrated in Table 1 could be correlated to other oral bacteria associated with oral disease. *S. Sobrinus*, another common pathogen associated with dental plaque is also associated with dental caries.

BHA, BHT, gallic acid, octyl gallate and *magnolia* bark extract (MBE) samples were dissolved in ethanol to produce 1-10% working solution and was added to a nutrient broth and shaken well and was diluted two-fold in individual test tubes A total of 0.2 mL of inoculated bacteria culture purchased from ATCC was added to each test tube. The tubes were incubated aerobically at 37° C. for 1-2 days. The MIC level was recorded as the lowest concentration of test compound that showed no visible growth.

TABLE 2

MIC and FIC values of MBE and common antioxidants *S. sobrinus*

| Sample | MIC (ppm) | FIC |
|---|---|---|
| MBE | 25 | — |
| BHA | 500 | — |
| BHT | >2000 | — |
| Gallic acid | >2000 | — |
| Octyl gallate | 250 | — |
| MBE/BHA (1:5) | 25/125 | 1.25 |
| MBE/BHT (1/10) | 6.5/62.5 | 0.26 |
| MBE/Gallic acid (1:10) | 25/250 | 1.0 |
| MBE/Octyl gallate (1:5) | 25/125 | 1.5 |

Interestingly, although similar in structure, BHA, gallic acid and octyl gallate did not demonstrate an enhanced effect with MBE against *S. sobrinus* with FIC values ranging from 1 to 1.5. However, MBE combined with BHT demonstrated a strong synergistic effect against *S. sobrinus*, having a FIC value of 0.26.

These results provide evidence that the present invention offers a unique, inexpensive, consumer friendly and readily available means for providing oral compositions that are antibacterially effective against *S. mutans*, the oral bacteria associated with dental caries.

II. Oral Compositions

Oral compositions useful in this invention contain an antibacterial-effective amount of an antioxidant and an extract of *Magnolia* combined with a suitable carrier. A suitable carrier typically is a food-acceptable or food contact acceptable material in which *magnolia* extract and antioxidant used in the invention may be incorporated or dispersed without adverse effect. A typical suitable carrier is a water-soluble solid or chewable solid such as a confectionery composition. Another suitable carrier is a dentifrice such as a past or powder. The term "confectionery composition" as used herein includes chewing gums, and orally soluble tablets, beads and lozenges. Saliva dissolves the lozenge or chewable gum product, and promotes prolonged contact with oral surfaces so that the delivery of the antibacterial agents in a lozenge tablet, bead or chewing gum form ensures that an adequate dosage of the active ingredients are delivered to the oral surface when the product is used. Or, the confectionery composition may be in the form of a coating, shell, film, syrup or suspension. Such delivery systems are well known to one of skill the art, and generally entail stirring active antibacterial agents into a warm base with flavor and non-cariogenic sweeteners.

In a preferred embodiment, an oral composition is a chewing gum composition which is suitable for chewing and which comprises 2% or greater, by weight of the composition, of elastomer. Extracts of *Magnolia* are stable in chewing gums over time, at least twelve weeks under accelerated conditions. In general, chewing gum compositions are chewed or masticated by consumers, the process by which food is mashed and crushed by teeth. Such chewing gum compositions can take a variety of shapes and forms, for example, a pellet, a gumball, a square, a stick, etc., and may be coated by a variety of materials including but not limiting to sugars, polyols, chocolates, syrups, films, and the like, alone or in any combination. Colors, high intensity sweeteners and flavors may also be added to the coating solution. For pellet or coated chewing gums, extracts of *Magnolia* may be incorporated in a coating rather than in a center.

A chewing gum useful in the present invention preferably is a sugarless chewing gum containing the antibacterial compounds. Chewing gum formulations typically contain, in addition to, a chewing gum base, one or more plasticizing agents, at least one sweetening agent and at least one flavoring agent.

Gum base materials suitable for use in the practice of this invention are well known in the art and include natural or synthetic gum bases or mixtures thereof. Representative natural gums or elastomers include chicle, natural rubber, jelutong, balata, guttapercha, lechi caspi, sorva, guttakay, crown gum, perillo, or mixtures thereof. Representative synthetic gums or elastomers include butadiene-styrene copolymers, polyisobutylene and isobutylene-isoprene copolymers. The gum base is incorporated in the chewing gum product at a concentration of about 10 to about 40 wt. % and preferably about 20 to about 35 wt. %.

Plasticizing/softening agents commonly used in chewing gum compositions are suitable for use in this invention, including gelatin, waxes and mixtures thereof in amounts of about 0.1 to about 5%. The sweetening agent ingredient used in the practice of this invention may be selected from a wide range of materials, and include the same artificial and polyol sweeteners used for the preparation of tablets, beads and lozenges. Polyol sweeteners such as sorbitol and malitol are present in the chewing gum composition of the present invention in amounts of about 40 to about 80 wt. % and preferably about 50 to about 75 wt. %. The artificial sweetener is present in the chewing gum composition of the present invention in amounts of about 0.1 to about 2 wt. % and preferably about 0.3 to about 1 wt. %.

The orally acceptable vehicle or carrier in a lozenge, bead or tablet is a non-cariogenic, solid water-soluble polyhydric alcohol (polyol) such as mannitol, xylitol, sorbitol, maltitol, erythritol, hydrogenated starch hydrozylate (HSH), hydrogenated glucose, hydrogenated disaccharides or hydrogenated polysaccharides, in an amount of about 85 to about 95 wt. % of the total composition. Emulsifiers such as glycerin, and tableting lubricants, in minor amounts of about 0.1 to 5 wt. %, may be incorporated into the tablet, bead or lozenge formulation to facilitate the preparation of the tablet beads and lozenges. Suitable lubricants include vegetable oils such as coconut oil, magnesium stearate, aluminum stearate, talc, starch and polyethylene glycols. Suitable noncariogenic gums include kappa carrageenan, carboxymethyl cellulose, hydroxyethyl cellulose and the like.

A lozenge, bead or tablet may optionally be coated with a coating material such as waxes, shellac, carboxymethyl cellulose, polyethylene/maleic anhydride copolymer or kappa-carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet, bead and lozenge compositions of this embodiment affords a relatively longer time period of contact of the teeth in the oral cavity with the antibacterial active ingredients of the present invention.

Preferably, an oral composition also includes a trigeminal stimulant to provide hot, cold, tingling or irritating effects in the oral cavity of a consumer thereby increasing uptake of the antibacterial compounds to provide oral health benefits.

In a preferred embodiment, an oral composition of this invention comprises a trigeminal stimulant or sensate including but not limited to menthol and other cooling compounds such as WS-23 and other cooling carboxamide compounds, camphor, allyl isothiocyanate, capsaicin, diallyl sulfide alone or in combination.

This invention is illustrated, but not limited by, the following Examples:

Example 1

A chewing gum formulation (designated "Compositions A, B & C") containing both *Magnolia* extract containing at least 90% by weight magnolol and at least 2% by weight honokiol combined with antioxidants which work with enhanced activity to kill or inhibit the growth of *S. mutans*:

| Ingredients | A Weight % | B Weight % | C Weight % |
| --- | --- | --- | --- |
| Gum Base | 26.00 | 26.00 | 23.50 |
| Sorbitol | 60.00 | 54.00 | 60.00 |
| Mannitol | 1.00 | — | 3.00 |
| Lycasin/Glycerin | 8.44 | 8.50 | 12.00 |
| Sweetener | 0.80 | 0.80 | 0.80 |
| Flavor | 1.75 | 1.75 | 1.75 |
| Magnolia Extract | 0.002 | 0.001 | 0.01 |
| BHA | 0.01 | — | — |
| Propyl Gallate | — | 0.001 | — |
| Octyl Gallate | — | — | 0.05 |

Example 2

A compressed tablet formulation (designated "Composition D") containing both *Magnolia* extract containing at least 90% by weight magnolol and at least 2% by weight honokiol combined with antioxidants that work synergistically to kill or inhibit the growth of *S. mutans*:

| Ingredients | D Weight % |
| --- | --- |
| Sorbitol | 97.43 |
| Magnesium Stearate | 1.00 |
| Magnolia Extract | 0.001 |
| Sweeteners | 1.00 |
| BHA | 0.005 |

Example 3

Composition A provides *magnolia* extract in a coating of the chewing gum composition, and BHA in the center of the chewing gum composition.

Example 4

Composition D provides *magnolia* extract in a coating of the compressed tablet composition, and BHA in the center.

The present invention is not limited to the above embodiments and can be variously modified. The above description of the preferred embodiments, including the Examples, is intended only to acquaint others skilled in the art with the invention, its principles, and its practical application so that others skilled in the art may adapt and apply the invention in its numerous forms, as may be best suited to the requirements of a particular use.

With reference to the use of the word(s) comprise or comprises or comprising in this entire specification (including the claims below), unless the context requires otherwise, those words are used on the basis and clear understanding that they are to be interpreted inclusively, rather than exclusively, and applicants intend each of those words to be so interpreted in construing this entire specification.

What is claimed is:

1. An oral chewable solid composition having synergistic antibacterial activity against *Streptococcus mutans* comprising an antibacterial-effective amount of an antioxidant selected from the group consisting of butylated hydroxyanisole, propyl gallate, octyl gallate, dodecyl gallate or combinations thereof, and an extract of *Magnolia* wherein the ratio of antioxidant to *Magnolia* extract is from about 1:1 to about 5:1.

2. The chewable solid composition of claim 1 wherein the extract of *Magnolia* comprises the compound magnolol.

3. The chewable solid composition of claim 1 wherein the extract of *Magnolia* comprises the compound honokiol.

4. The chewable solid composition of claim 2 wherein the magnolol comprises greater than 90% by weight of the extract.

5. The chewable solid composition of claim 3 wherein the honokiol comprises less than 50% by weight of the extract.

6. The chewable solid composition of claim 1 in which the antioxidant and extract of *Magnolia* has a fractional inhibitory concentration (FIC) of less than 1 against *Streptococcus mutans*.

7. The chewable solid composition of claim 1 wherein the chewable solid composition is a mint, chewing gum, chewy candy, or combinations thereof.

8. An antibacterial chewing gum composition having synergistic antibacterial activity against *Streptococcus mutans* comprising a combination of an antioxidant selected from the group consisting of butylated hydroxyanisole, propyl gallate, octyl gallate, dodecyl gallate, or combinations thereof and an extract of *Magnolia* wherein the extract comprises at least 80% by weight magnolol and wherein the ratio of antioxidant to *Magnolia* extract is about 5:1.

9. The composition of claim 8 wherein the antioxidant is selected from the group consisting of propyl gallate, octyl gallate, dodecyl gallate, or combinations thereof.

10. The composition of claim 8 wherein the antioxidant is octyl gallate, butylated hydroxyanisole, or combinations thereof.

11. The composition of claim 8 wherein the effective amount of antioxidant is from about 0.002 to about 2% by weight.

12. A method of inhibiting the growth of *Streptococcus mutans* by contacting with a chewable solid composition comprising a synergistic antibacterial effective amount of a combination of an antioxidant selected from the group consisting of butylated hydroxyanisole, propyl gallate, octyl gallate, dodecyl gallate, or combinations thereof, and an extract of *Magnolia* containing hydroxybiphenyl compounds selected from the group consisting of magnolol, honokiol and mixtures thereof, wherein the ratio of antioxidant to *Magnolia* extract is about 5:1.

13. The method of claim 12 in which the chewable solid composition contains an effective amount of *Magnolia* extract of 0.001 to about 5% by weight containing hydroxybiphenyl compounds of about 0.002 to about 2%, and the hydroxybiphenyl compounds contain 80% to about 99% by weight magnolol and 1 to 20% by weight honokiol.

14. An oral chewable solid composition having synergistic antibacterial activity against *Streptococcus sobrinus* comprising an antibacterial-effective amount of butylated hydroxytoluene and an extract of *Magnolia*.

15. The composition of claim 8 wherein the effective amount of the *Magnolia* Extract is in the range of 0.001 to about 5% by weight.

16. The composition of claim 14, wherein the ratio of butylated hydroxytoluene to *Magnolia* extract is about 10:1.

17. The composition of claim 1, wherein the ratio of antioxidant to *Magnolia* extract is about 5:1.

* * * * *